United States Patent [19]

Cecco et al.

[11] Patent Number: 5,049,817
[45] Date of Patent: Sep. 17, 1991

[54] EDDY CURRENT PROBE, INCORPORATING MULTI-BRACELETS OF DIFFERENT PANCAKE COIL DIAMETERS, FOR DETECTING INTERNAL DEFECTS IN FERROMAGNETIC TUBES

[75] Inventors: Valentino S. Cecco; F. Leonard Sharp, both of Deep River, Canada

[73] Assignee: Atomic Energy of Canada Limited, Ottawa, Canada

[21] Appl. No.: 535,522

[22] Filed: Jun. 8, 1990

[51] Int. Cl.⁵ .................... G01N 27/90; G01R 33/12
[52] U.S. Cl. ................................. 324/220; 324/225; 324/232
[58] Field of Search .................... 324/219–221, 324/225, 232, 242, 243

[56] References Cited

U.S. PATENT DOCUMENTS

| 2,124,579 | 7/1938 | Knerr et al. | 324/242. X |
| 4,808,924 | 2/1989 | Cecco et al. | 324/220 |
| 4,808,927 | 2/1989 | Cecco et al. | 324/220 |
| 4,855,677 | 8/1989 | Clark, Jr. et al. | 324/232 X |

FOREIGN PATENT DOCUMENTS 0017353 2/1983 Japan .................................. 324/232

Primary Examiner—Gerard R. Strecker
Attorney, Agent, or Firm—Gowling, Strathy & Henderson

[57] ABSTRACT

Eddy current probes for detecting internal defects in a ferromagnetic tube are disclosed. The probe uses a plurality of eddy current measuring means, each being operated at a different operating point on the impedance diagram. By operating more than one such eddy current measuring means simultaneously, noises by, for example, permeability variation of a ferromagnetic material and internal magnetic deposit, can be made less influential.

12 Claims, 3 Drawing Sheets

EDDY CURRENT PROBE, INCORPORATING MULTI-BRACELETS OF DIFFERENT PANCAKE COIL DIAMETERS, FOR DETECTING INTERNAL DEFECTS IN FERROMAGNETIC TUBES

FIELD OF THE INVENTION

This invention relates to an eddy current probe for detecting localized defects in a tube made of a ferromagnetic material. More specifically, the invention relates to a ferromagnetic tube inspection technique which utilizes an eddy current probe operating at two operating points in the impedance diagram.

BACKGROUND OF THE INVENTION

Eddy current testing is a non-destructive test technique based on inducing electrical currents in the material being inspected and observing the interaction between these currents and the material. Eddy currents are generated by electromagnetic coils in the test probe, and monitored simultaneously by measuring probe electrical impedance. Since it is an electromagnetic induction process, direct electrical contact with the sample is not required; however, the sample material must be electrically conductive.

Various eddy current probes have been proposed for inspecting cylindrical or tubular components. Among many variations, the self-inductance type (the absolute and differential) and the transmit-receive type are in wide use. Many different coil configurations are also practised. Both ferromagnetic and non-ferromagnetic materials can be inspected. However, special care must be exercised for inspecting defects as will be discussed later.

In the past, bodies of ferromagnetic material have been inspected by a method such as the flux leakage method as taught, for example, in U.S. Pat. Nos. 3,091,733 (May 28, 1963, Fearon et al), 4,468,619 (Aug. 28, 1984, Reeves), and 4,602,212 (July 22, 1986, Hiroshima et al). In this method, the metal is magnetized in a direction parallel to its surface. At defects or where regions of the metal body are not uniform, some magnetic flux passes into the air and may be detected by sensors located nearby, thus giving an indication of the presence of faults, non-uniformity, etc.

U.S. Pat. No. 4,107,605 (Aug. 15, 1978, Hudgell) discloses an eddy current technique for detecting abnormalities in a pipeline of a ferromagnetic material. The eddy current probe includes a plurality of spiral sensing coils placed with their axes normal to the surface of the pipeline wall and connected on four legs of an AC bridge, thus compensating for lift-off. A biasing magnetic field by a permanent magnet permits distinguishing internal from external defects in weakly ferromagnetic tubes by comparing outputs from systems with and without biasing field.

U.S. Pat. Nos. 3,952,315 (Apr. 20, 1976, Cecco) and 2,964,699 (Dec. 6, 1960, Perriam) describe eddy current probes for use of testing weakly ferromagnetic tubes. They both include magnetic saturation means.

In U.S. Pat. Nos. 2,992,390 (July 11, 1961, de Witte) and 3,940,689 (Feb. 24, 1976, Johnson, Jr.) special electromagnetic ways of generating magnetic fields are taught in connection with the eddy current testing in that de Witte uses uniquely designed cores for transmit-receive coils using multiple test frequencies and Johnson, Jr. employs a solenoid wound about a core of a substantial length.

U.S. Pat. No. 3,437,810 (Apr. 8, 1969, Wood et al) describes a tube inspection apparatus having several different inspection instruments, one of which is an eddy current probe using two test frequencies.

None of these patents, however, is concerned with benefits obtained in operating simultaneously a plurality of eddy current probes at more than one operating point of the impedance diagram.

OBJECTS OF THE INVENTION

It is therefore an object of the present invention to provide an eddy current probe for inspecting ferromagnetic tubes which is sensitive to internal defects but relatively immune to noises.

It is therefore another object of the present invention to provide an eddy current probe for inspecting ferromagnetic tubes which includes two or more eddy current measuring means, each operating at a different operating point of the impedance diagram.

It is thereafter a further object of the present invention to provide an eddy current probe which is less susceptible to permeability noises.

SUMMARY OF THE INVENTION

Briefly stated, in accordance with the present invention, an eddy current probe for detecting internal defects in a tube made of a ferromagnetic material, includes a probe housing made of a non-ferromagnetic material and shaped to be introduced into the tube for inspection. The housing has an axis substantially coinciding with the axis of the tube under inspection when the probe is in use. The probe further includes a first bracelet provided in the housing and carrying a plurality of first pancake coils in a ring the said first coils are of a first diameter and operated at a first RF frequency. The probe still further has a second bracelet provided in the housing adjacent to the first bracelet and carrying a plurality of second pancake coils in a circle, the second coils are of a second diameter larger than the first diameter and operated at a second RF frequency higher than the first RF frequency.

BRIEF DESCRIPTION OF THE DRAWINGS

In a more complete understanding of the present invention and for further objects and advantages thereof, references may be made to the following description taken in conjunction with the accompanying drawings in which.

DETAILED DESCRIPTION OF THE PREFERRED EMBODIMENTS

Eddy current testing detects changes in eddy current induced in an object under test and is sensitive to material properties of the object through their effect on resistivity and magnetic permeability. The eddy current is indirectly measured by a probe coil located near the surface of the object which monitors the magnetic flux created by the eddy current. However, when an eddy current probe is used for ferromagnetic tube inspection, the magnetic permeability of the ferromagnetic material affects the probe coils inductance as well as depth of eddy current penetration into the material. The magnetic permeability strongly depends on factors such as:

thermal processing history;
mechanical processing history;
chemical composition;
internal stresses; and
temperature (if close to Curie temperature).

The large variations in permeability make conventional eddy current testing for defects in magnetic materials very difficult. Thus, it is not that the eddy current probe is insensitive to a ferromagnetic material, but that it produces signals from defects as well as from permeability variation of the material. It is very difficult to analyze and separate defect signals from permeability variations (permeability noise). One way of suppressing the permeability noise is to bring the magnetic material to a condition where $\mu_r = 1.0$. Relative incremental or recoil permeability, $\mu_r$, is defined as $\mu_r = \Delta B/\Delta H$ where $\Delta B$ is the change in flux density which accompanies a change in magnetizing force, $\Delta H$ created for example by an eddy current coils' alternating current.

A few slightly magnetic materials can be heated above their Curie temperature to make them nonmagnetic. Monel (TM) 400 heated to between 50° and 70° C. has been tested in this manner. Most materials, however, have too high a Curie temperature to be tested by this approach. The only other way to decrease $\mu_r$ to unity is by magnetic saturation.

The inventors have now come up with a new way of distinguishing desired signals from permeability noise and magnetite deposits.

Figure 1:
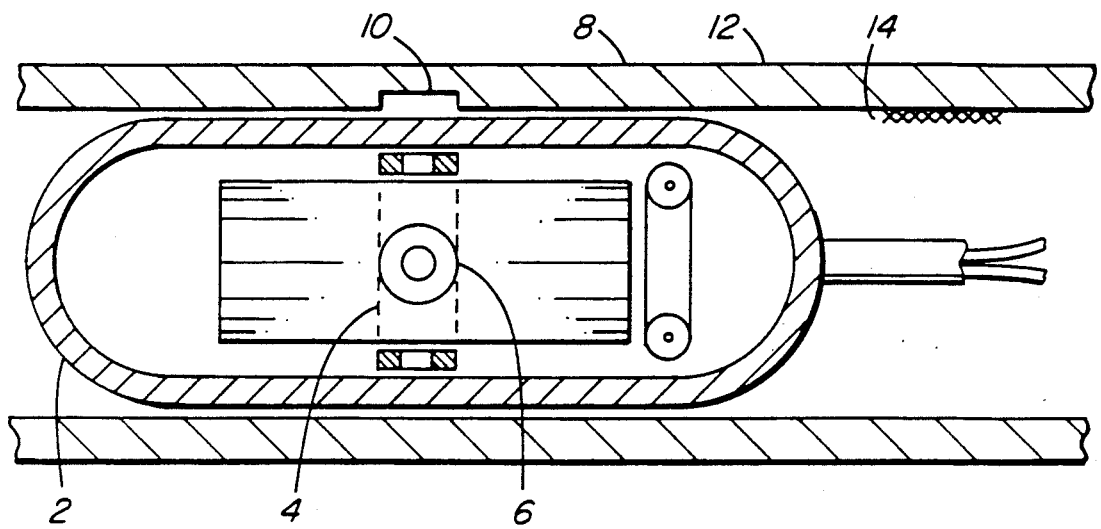
FIG. 1 is a schematic view of a prior art eddy current probe, showing some typical anomalies.

FIG. 1 illustrates schematically a known eddy current probe in use for detecting defects in a ferromagnetic tube. The probe 2 carries a bracelet 4 of more than one pancake coils 6 positioned in a circle. The tube 8 under test includes a groove 10 on the inside wall and permeability variation 12 in the wall for illustration. It also shows magnetite deposits 14.

Figure 2:
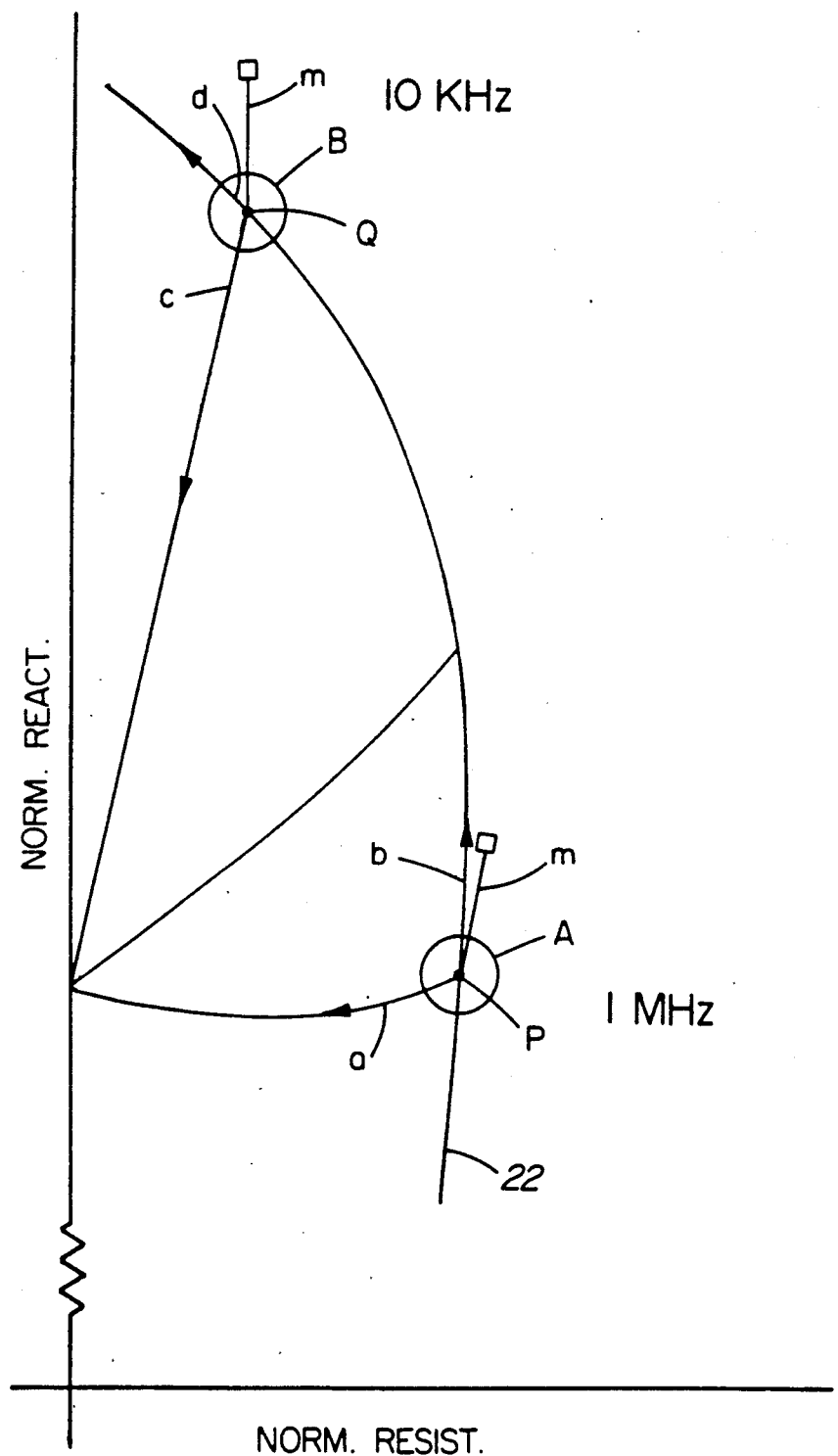
FIG. 2 is an impedance diagram of an eddy current probe used for a ferromagnetic inspection.

The operations of the probe will be described now by referring to an impedance diagram of an eddy current probe when in operation adjacent a test sample, as shown in FIG. 2, wherein, the horizontal axis is the normalized resistance and the vertical axis the normalized reactance. It has been recognized in ferromagnetic testing that to measure magnetic permeability and resistivity (of a test sample) in the presence of lift-off signal, probe size and test frequency should be chosen to operate at a point P in region marked A. In the diagram an increase in permeability and/or resistivity produces a signal upward along the line 22, and a decrease—a signal downward.

On the other hand it is also known that for measuring internal defects in the presence of permeability variation, the operating point Q in region B near the top of the impedance diagram is chosen.

In these operations, various conditions influence certain signals and make it difficult to discriminate each signal. The present invention facilitates a solution to this problem and enables to interpret signals for detection of internal defects in a ferromagnetic tube.

Thus, as seen in FIG. 2, a first test is carried out with a probe operating at a point Q in region B near the top of the impedance diagram which produces following signals. The magnetite signal m is generated by magnetite on the tube surface. A lift-off produces a lift-off signal c and a change in permeability produces a permeability signal d. The signals c and m are nearly in opposite phase, thus making it difficult to interpret them correctly. On the other hand, while it is small in amplitude, the signal d is out-of-phase with the other signals and is therefore possible to discriminate from the other signals.

Now, in region A, a lift-off (separation of the probe from the tube surface) produces a lift-off signal a and a change in the permeability ($\Delta \mu_r$) produces a permeability signal b. The lift-off signal a contains not only an indication of lift-off but also an indication of internal defects in the tube. The eddy current signal is also caused not only by permeability variation (permeability noise) of the material of the tube but also by the presence of magnetite deposits. This presence of some foreign magnetic materials (collectively called magnetite) on the tube surface produces a magnetite signal indicated by m. At the operating point P, this signal m is very close in phase to the signal b. Therefore, the signals caused by permeability change and the magnetite are easily separated from the lift-off signal because they are 90° out-of-phase to one another.

The result of the second test permits an interpretation of the signals of the first test caused by lift-offs or magnetite deposits.

Figure 3:
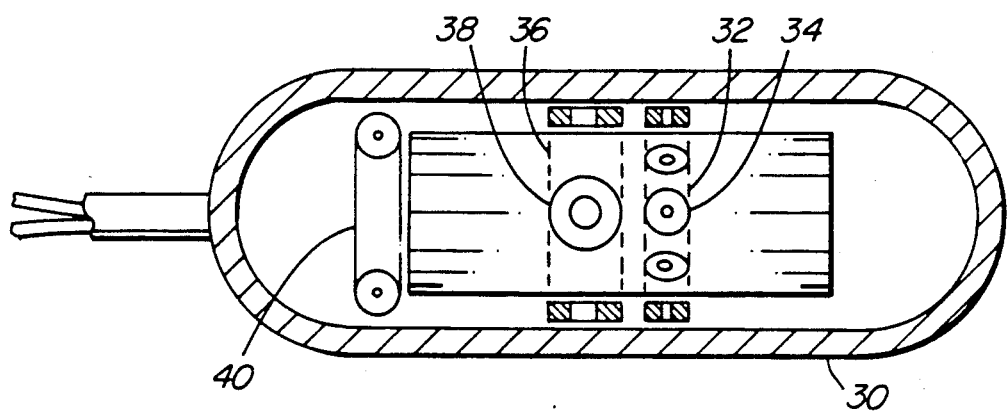
FIG. 3 is a schematic view of an eddy current probe according to one embodiment of the present invention.

Referring to FIG. 3, there is illustrated schematically an eddy current probe for ferromagnetic tube inspection according to one embodiment of the present invention which carries out the two tests. The probe 30 carries a pair of closely located bracelets of pancake coils. The first bracelet 32 contains, in this embodiment, eight pancake coils 34 of a first diameter and the second bracelet 36 has four pancake coils 38 of a second diameter. A toroidal coil 40 is a common reference coil needed for the pancake coils operating as absolute probes. The first bracelet of coils is designed to operate in region B of the impedance diagram while the second bracelet is in region A. The two bracelets are operated simultaneously to generate signals on a display so that correlation of the signals with respect to a test location can be carried out.

Thus the first bracelet produces a signal indicative of magnetites, defects and lift-offs, while the second bracelet generates separable signals, one indicative of magnetites and permeability variation and another of lift-offs and defects. By analyzing all of these signals, it is possible to determine the presence of anomalies.

The coil diameter and the test frequency determine the operating point. However in selecting the frequency, the skin depth limitations must also be taken into account, i.e. it is preferable to have the test frequency not differing too much for the operating points. Therefore, in a way of typical example, the first bracelet operates at a frequency lower than about 50 KHz and the second bracelet at a frequency higher than about 200 KHz and the second diameter is twice as large as the first diameter. Other combinations of the test frequency and the coil diameter can be chosen to set operating points to suit specific testings. It is therefore possible to use a same frequency for both bracelets but different coil diameters as long as two appropriate operating points are utilized.

There are various coil configurations which can be used for the present invention as further embodiments.

Figure 4:
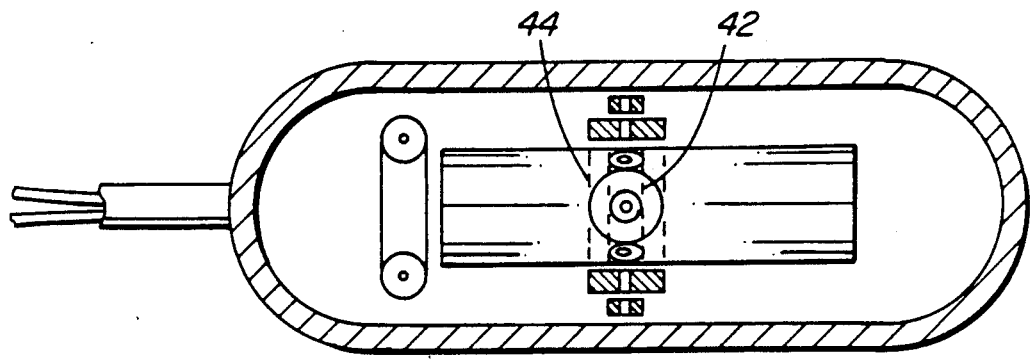
FIG. 4 is a schematic view of an eddy current probe according to a further embodiment of the present invention.

FIG. 4 shows one of such embodiments in that the first and second bracelet of coils are located at the same axial position. Because of the presence of the first bracelet 42, the second bracelet 44 would have less magnetic coupling with the tube which would lower the sensitivity. However the correlation of testing sites is more accurate.

The coils in the bracelets can be all polarized in the same direction. However, as further embodiments, the coils in one bracelet can be polarized alternately to effect circumferential compensation and 100% coverage of the tube.

Figure 5:
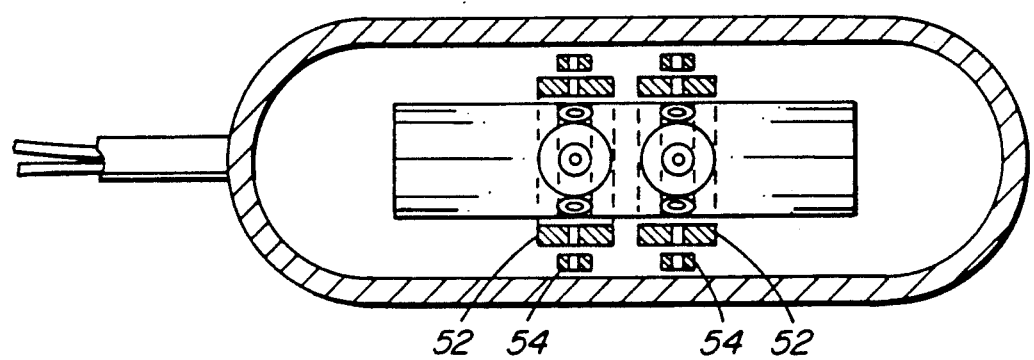
FIGS. 5 and 6 are schematic views of an eddy current probe according to yet other embodiments of the present invention.

FIG. 5 illustrates another embodiment of the present invention in that the coils are connected in the differential configuration. Thus a pair of identical first and second bracelets 52 and 54 are provided adjacent to one another to perform a differential testing.

Figure 6:
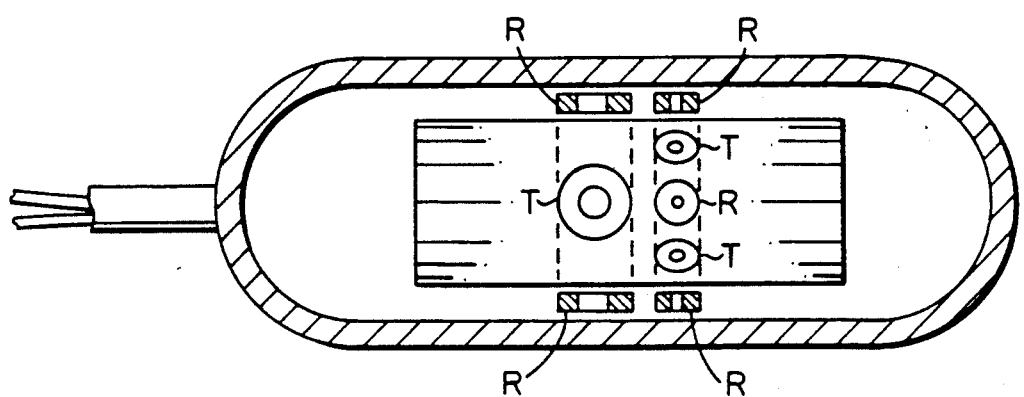

In FIG. 6, yet another embodiment is schematically illustrated. In the embodiment, a transmit-receive configuration of an eddy current probe is used. In each of bracelets 1 and 2, R and T indicate receive coils and transmit coils, respectively. As in previous embodiments, the first bracelet contains eight smaller coils and operates at a lower frequency. All the coils in each bracelet are electromagnetically polarized in the same radial direction.

We claim:

1. An eddy current probe for detecting internal defects in a tube made of a ferromagnetic material, comprising:
    a probe housing made of a non-ferromagnetic material and shaped to be introduced into the tube for inspection, said housing having a central axis substantially coinciding with the axis of the tube under inspection when the probe is in use;
    first and second bracelets, having inner and outer surfaces, provided in said housing, wherein said bracelets are essentially concentric with said central axis of said housing;
    said first bracelet carrying, on said outer surface thereof, a plurality of first pancake coils arranged in a ring about said central axis of said housing, the said first coils being of a first diameter and operated at a first RF frequency; and
    said second bracelet being adjacent to said first bracelet and carrying, on said outer surface thereof, a plurality of second pancake coils arranged in a ring about said central axis of said housing, said second coils being a second diameter larger than said first diameter and operated at a second frequency equal to or higher than said first RF frequency.

2. The eddy current probe according to claim 1 wherein:
    the said first bracelet carries eight pancake coils being operated at the said first RF frequency which is lower than about 50 KHz; and
    the said second bracelet carries four pancake coils being operated at the said second RF frequency which is higher than about 200 KHz.

3. The eddy current probe according to claim 2 wherein:
    the said first bracelet is located outside the said second bracelet concentrically therewith.

4. The eddy current probe according to claim 2 wherein:
    the said second diameter is at least twice as large as the said first diameter.

5. The eddy current probe according to claim 3 wherein:
    the said second diameter is at least twice as large as the said first diameter.

6. The eddy current probe according to claim 4 wherein:
    the said first and second pancake coils are electromagnetically alternately polarized within their bracelet.

7. The eddy current probe according to claim 5 wherein:
    the said first and second pancake coils are electromagnetically alternately polarized within their bracelet.

8. The eddy current probe according to claim 3 further comprising:
    pairs of the first and the second bracelets positioned adjacent to one another to form a differential configuration.

9. The eddy current probe according to claim 4 further comprising:
    pairs of the first and the second bracelets positioned adjacent to one another to form a differential configuration.

10. The eddy current probe according to claim 2 wherein:
    in each of the said two bracelets, half the number of coils are connected to a transmitter and the remaining half to a receiver.

11. The eddy current probe according to claim 3 wherein:
    in each of the said two bracelets, half the number of coils are connected to a transmitter and the remaining half to a receiver.

12. The eddy current probe according to claim 5 wherein:
    in each of the said two bracelets, half the number of coils are connected to a transmitter and the remaining half to a receiver.

* * * * *